US00PP30178P3

(12) United States Plant Patent
Suphachadiwong

(10) Patent No.: US PP30,178 P3
(45) Date of Patent: Feb. 5, 2019

(54) ***VANDA* PLANT NAMED 'SPCDW1519'**

(50) Latin Name: ***Vanda* Jones ex R. Br.**
Varietal Denomination: SPCDW1519

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 79 days.

(21) Appl. No.: 15/530,042

(22) Filed: Nov. 23, 2016

(65) Prior Publication Data

US 2017/0156249 P1 Jun. 1, 2017

(30) Foreign Application Priority Data

Nov. 27, 2015 (QZ) ..... PBR 2015/2870

(51) Int. Cl.
*A01H 5/02* (2018.01)

(52) U.S. Cl.
USPC ..... Plt./311

(58) Field of Classification Search
USPC ..... Plt./311
See application file for complete search history.

*Primary Examiner* — Keith O. Robinson
(74) *Attorney, Agent, or Firm* — Samuel R. McCoy, Jr.

(57) ABSTRACT

A new and distinct *Vanda* cultivar named 'SPCDW1519' which is characterized by long, dark green foliage with large flowers borne on a tall inflorescence, purple sepals and petals with dark purple to red-purple reticulate venation, a dark red-purple labellum, and the stability of these characteristics from generation to generation.

4 Drawing Sheets

Latin name of the genus and species: The Latin name of the genus and species of the novel variety disclosed herein is *Vanda* Jones ex R. Br.

Variety denomination: The inventive variety of *Vanda* disclosed herein has been given the variety denomination 'SPCDW1519'.

CROSS REFERENCE TO RELATED APPLICATIONS

This application claims priority to the Community Plant Variety Rights application number 2015/2870, filed Nov. 27, 2015, which is herein incorporated by reference.

BACKGROUND OF THE INVENTION

Parentage: The *Vanda* variety 'SPCDW1519' is the result of a planned breeding program. The new variety originated as a seedling from the crossing of *Vanda* 'MNSR' (not patented), the seed parent, with *Vanda* '70BL' (not patented), the pollen parent. Both parents were developed by, and are owned by, the inventor and were never commercially released. The crossing was made by the inventor in his research greenhouse in Bangphra, Thailand in August of 1996.

The new variety was first selected in December of 2000, in a research greenhouse in Bangphra, Thailand belonging to the inventor. After identifying the new variety as a potentially interesting selection, the inventor continued confidential testing and propagation of 'SPCDW1519', assessing stability of the unique characteristics of this variety.

Asexual Reproduction: Asexual reproduction of the new cultivar 'SPCDW1519', by way of mericloning, was first initiated in September of 2010 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1519' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1519'. These characteristics in combination distinguish 'SPCDW1519' as a new and distinct *Vanda* cultivar:

1. *Vanda* 'SPCDW1519' exhibits large flowers borne on a tall inflorescence; and
2. *Vanda* 'SPCDW1519' exhibits long, dark green foliage; and
3. *Vanda* 'SPCDW1519' exhibits purple sepals and petals with dark purple to red-purple reticulate venation; and
4. *Vanda* 'SPCDW1519' exhibits a dark red-purple labellum.

BOTANICAL DESCRIPTION OF THE PLANT

Figure 1:
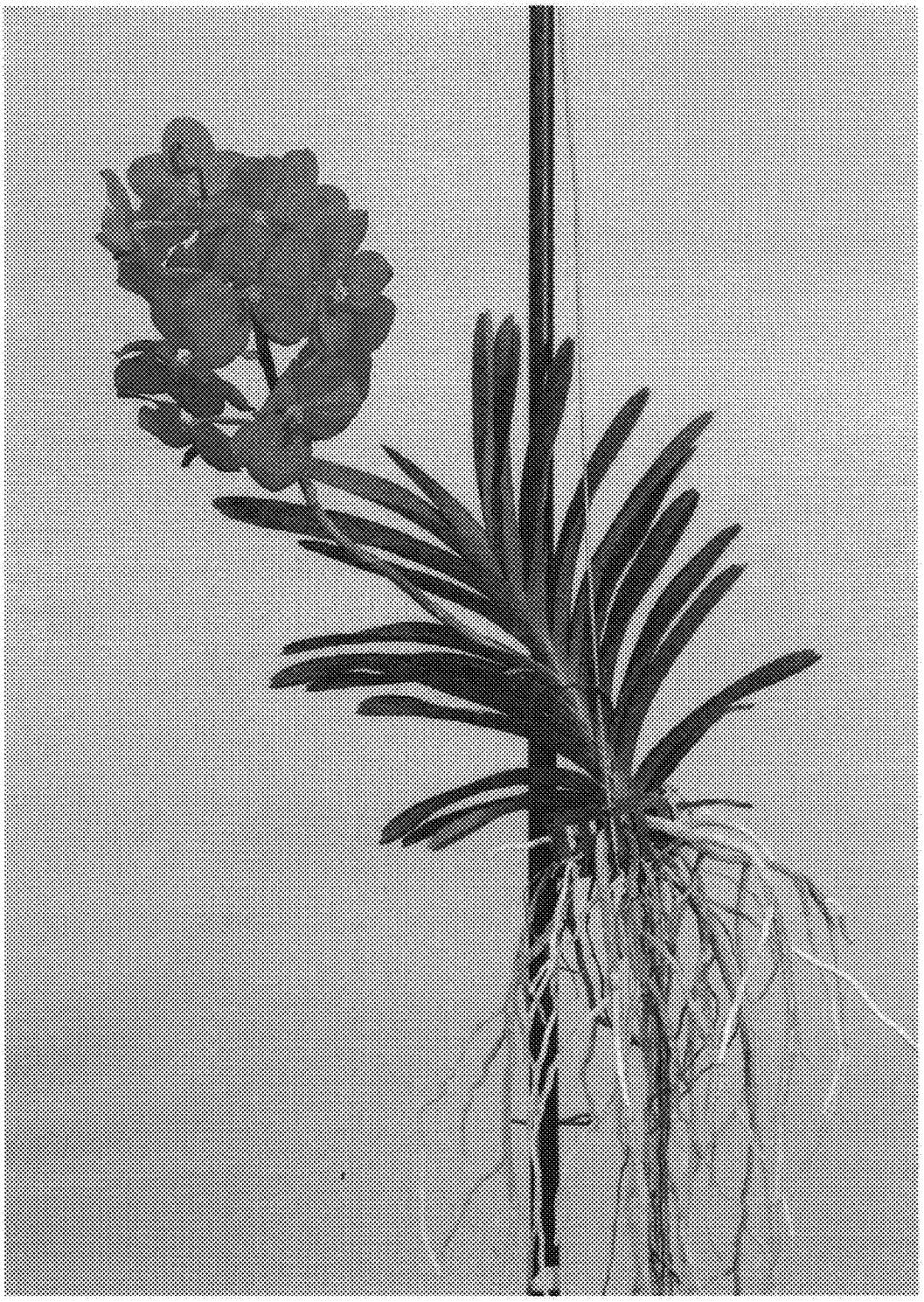
FIG. 1 illustrates, as nearly true as it is reasonably possible to make the same in color photographs of this type, an exemplary plant of 'SPCDW1519' grown in a commercial greenhouse in Honselersdijk, the Netherlands. This plant is approximately 6 years old from the time of mericloning, shown planted in an 8 by 8 cm container.
Figure 2:
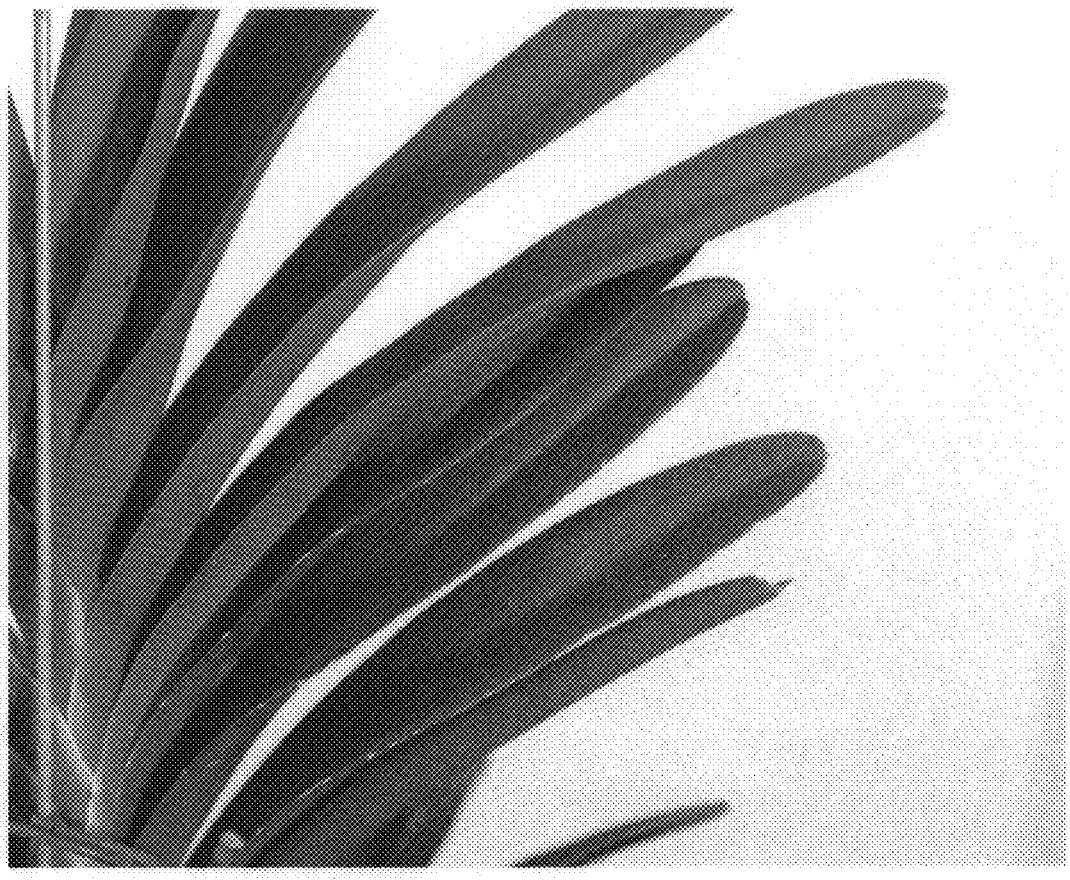
FIG. 2 illustrates, as nearly true as it is reasonably possible to make the same in color photographs of this type, the typical foliage of 'SPCDW1519'.
Figure 3:
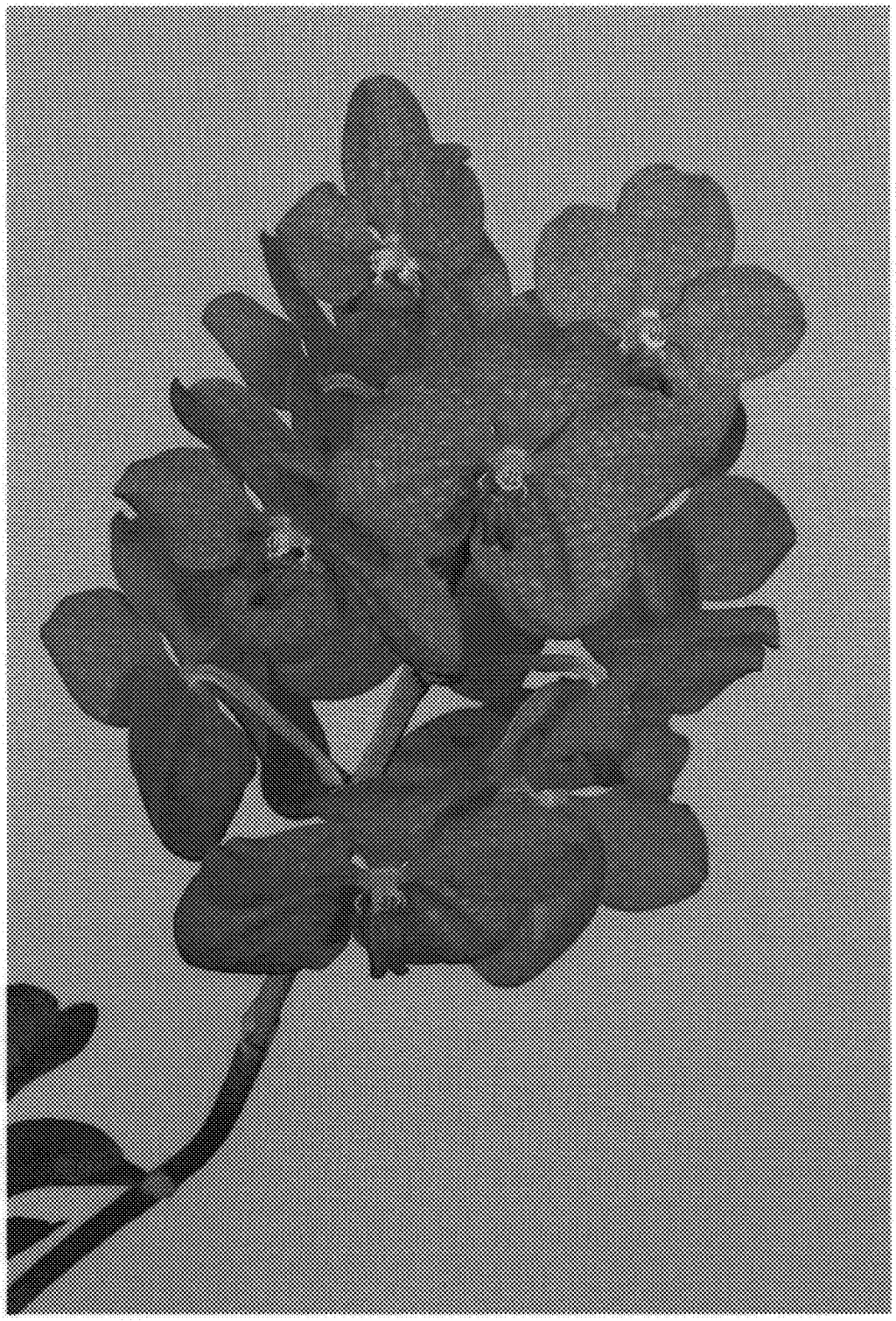
FIG. 3 illustrates, as nearly true as it is reasonably possible to make the same in color photographs of this type, the typical inflorescence of 'SPCDW1519'.
Figure 4:
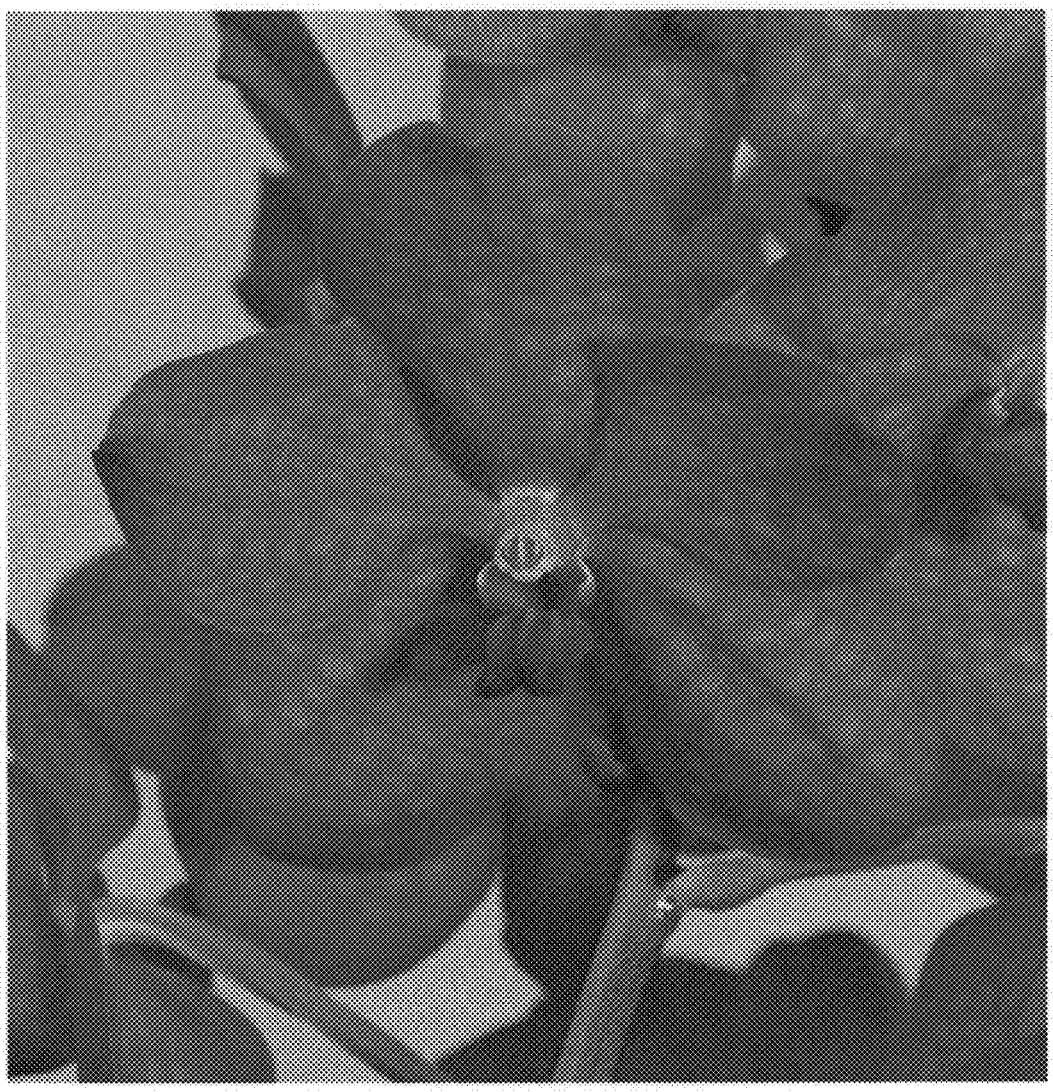
FIG. 4 illustrates, as nearly true as it is reasonably possible to make the same in color photographs of this type, the typical flower of 'SPCDW1519'.

The following observations and measurements made in October of 2016 describe averages from a sample set of six specimens of six year-old 'SPCDW1519' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1519' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1519' and comparisons with other varieties of *Vanda* are provided below.

Plant description:

- *Growth habit*.—Perennial; monopodial, upright. Single monopodial leafy stem, with flowers carried slightly above the leaf plane; inflorescences growing from the leaf axils.
- *Average height from base (plant grown in hanging basket, so no soil line present) to foliar plane*.—35.0 cm.
- *Average height from base (plant grown in hanging basket, so no soil line present) to top of floral plane*.—52.1 cm.
- *Plant spread*.—Average of 35.0 cm.
- *Appropriate container size*.—8 cm by 2 cm rectangular hanging basket.
- *Growth rate*.—Moderate.
- *Plant vigor*.—Moderate.
- *Propagation type*.—Meristematic tissue culture propagation using the base of the leaves.
- *Propagation details*.—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.
- *Disease and pest resistance or susceptibility*.—Plants have not been observed to be susceptible or resistant to pathogens and pests common to *Vanda*.
- *Environmental tolerances*.—Adapt to, at least, USDA Zones 11 and 12 and temperatures as high as 40 degrees Celsius; high tolerance to rain; moderate to high tolerance to wind.

Root system:

- *General*.—Moderately dense rooting; with aerial roots only.
- *Dimensions, mature roots*.—78.9 cm long with a diameter of 0.5 cm, on average.
- *Texture*.—Very fleshy; non-fibrous.
- *Color*.—Greyed-green, in between RHS 192A and 192B; root apex is yellow-green, RHS 146A.

Stem:

- *Branching habit*.—Monopodial; no lateral branches present.
- *Number of primary (main) stems per plant*.—One.
- *Number of secondary (lateral) branches per plant*.—None.
- *Appearance and shape*.—Circular, formed by the leaf sheaths.
- *Length*.—17.8 cm.
- *Diameter*.—1.1 cm.
- *Internode length*.—1.0 cm.
- *Luster*.—Matte.
- *Aspect, main stem*.—Near vertical.
- *Strength*.—Very strong.
- *Color, juvenile*.—Yellow-green, in between RHS 145C and 145D.
- *Color, mature*.—Yellow-green, in between RHS 145C and 145D.
- *Color at internodes*.—Yellow-green, in between RHS 145C and 145D.
- *Pubescence*.—Glabrous.

Foliage:

- *Arrangement*.—Distichous.
- *Dimensions*.—21.0 cm long, excluding the sheath, and 2.8 cm wide.
- *Shape of blade*.—Ligulate; moderately carinate.
- *Aspect*.—Moderately curved.
- *Apex*.—Unequal praemorse.
- *Base*.—Sheathing.
- *Sheath dimensions*.—3.3 cm long and 1.1 cm wide, on average.
- *Sheath color*.—Yellow-green, in between RHS 145B and 145C.
- *Margin*.—Entire.
- *Pubescence, texture and luster of adaxial surface*.—Glabrous, smooth, and matte.
- *Pubescence, texture and luster of abaxial surface*.—Glabrous, smooth, and matte.
- *Color*.—Variegation — Absent. Juvenile foliage, adaxial surface — Green, nearest to RHS 143A. Juvenile foliage, abaxial surface — Green, nearest to RHS 143A. Mature foliage, adaxial surface — Green, nearest to RHS NN137A. Mature foliage, abaxial surface — Yellow-green, RHS 146B.
- *Venation*.—Parallel.
- *Venation color, adaxial surface*.—Green, nearest to RHS NN137A.
- *Venation color, abaxial surface*.—Yellow-green, RHS N144A.
- *Petiole*.—No petioles present; leaves sessile.

Inflorescence:

- *Inflorescence arrangement*.—Axially placed raceme.
- *Natural flowering season*.—Autumn into winter.

*Time to flower*.—Approximately 10 months.

*Quantity of inflorescence per plant*.—One.

*Flowers per inflorescence*.—Average of 12.

*Flowers per plant*.—11 open flowers and 1 flower buds.

*Inflorescence height*.—Approximately 23.0 cm (measured from base of lowest flower to top of upper flower).

*Inflorescence diameter*.—Approximately 18.4 cm.

*Peduncle*.—Dimensions — Approximately 40.9 cm long and 0.7 cm wide. Aspect — Generally at a 40 degree angle to lateral branch axis. Strength — Moderately strong. Texture and luster — Glabrous and moderately glossy. Color — Yellow-green, nearest to RHS 144A.

Bud:

*Length*.—Average of 1.3 cm.

*Diameter*.—Average horizontal diameter is 1.2 cm; the vertical diameter is 1.8 cm.

*Shape*.—Cubic, with a deltoid apex which is pointed downward.

*Pubescence, texture and luster*.—Glabrous, smooth and slightly glossy.

*Color*.—Greyed-green, nearest to RHS N186D, and suffused with yellow green towards the base, nearest to RHS 145B.

Flower:

*Flower type*.—Zygomorphic (orchidaceous), typical shape for the genus *Vanda*.

*Flowering habit*.—Moderate.

*Shape*.—Zygomorphic, single; consisting of three sepals and three petals, one of which is transformed into a labellum; the two lateral petals slightly overlapping the dorsal sepal and slightly to moderately overlapping the lateral sepals; sepals do not overlap one another.

*Aspect*.—Flowers are outward-facing to slightly nodding.

*Vertical height*.—Approximately 9.7 cm.

*Diameter*.—Approximately 9.0 cm.

*Depth*.—Approximately 3.3 cm.

*Fragrance*.—No fragrance.

*Lastingness*.—3 weeks, on average.

*Persistent*.—Self-cleaning.

*Petals*.—Quantity of Petals — Three unfused petals; two conventional petals and one labellum. Arrangement — One lateral petal on each side. Length — Approximately 4.5 cm. Width — Approximately 4.8 cm. Shape — Broad ovate to near orbicular. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — Purple, nearest to RHS N78A; heavily dotted and blotched with a lighter shade of purple, nearest to RHS 77B. Color when opening, lower surface — Purple, nearest to RHS N78A; heavily dotted and blotched with a lighter shape of purple, nearest to RHS N78B. Color when fully opened, upper surface — Purple, nearest to RHS N78B. Color when fully opened, lower surface — Purple, nearest to RHS N78B. Fading, upper surface — Not fading. Fading, lower surface — Not fading. Venation — Densely reticulate. Venation color, fully opened, upper surface — Purple, in between RHS N78A and NN78A. Venation color, fully opened, lower surface — Purple, nearest to RHS NN78A.

*Labellum*.—Shape — Three-lobed; the shape of the lateral lobes is broad ovate, and the aspect is involute; the shape of the central lobe is narrow triangular to near oblong, and the aspect is revolute. Length — Central lobe — Approximately 2.0 cm. Lateral lobes — Approximately 0.7 cm. Width — Central lobe — Approximately 1.0 cm. Lateral lobes — Approximately 0.5 cm. Apex — Central lobe — Strongly emarginate. Lateral lobes — Emarginate. Base — Central lobe — Cuneate. Lateral lobes — Cuneate. Margin — Central lobe — Entire; not undulate. Lateral lobes — Entire; not undulate. Texture and luster of upper surface — Central lobe — Glabrous, velvety, and matte. Lateral lobes — Glabrous, velvety, and matte. Texture and luster of lower surface — Central lobe — Glabrous, velvety, and matte with the exception of the apex which is glossy. Lateral lobes — Glabrous, velvety, and matte. Color when opening, upper surface — Central lobe — Greyed-purple, nearest to RHS N186D, and suffused with red-purple towards the base, nearest to RHS 61A. Lateral lobes — Red-purple, nearest to RHS 67B; apex is white, RHS 155A. Color when opening, lower surface — Central lobe — Red-purple, nearest to RHS 64A, and fading to a lighter shade of red-purple towards the base, nearest to RHS 64C. Lateral lobes — Red-purple, a mixture of RHS 70B and 70D; apex is white, RHS 155A. Color when fully opened, upper surface — Central lobe — Greyed-purple, in between RHS N186C and N186D, and suffused with red-purple towards the base, nearest to RHS 61A. Lateral lobes — Red-purple, a mixture of RHS 70B and 70D; apex is white, RHS 155A. Color when fully opened, lower surface — Central lobe — Red-purple, nearest to RHS 64A, and fading to a lighter shade of red-purple towards the base, in between RHS 72B and 72C. Lateral lobes — Red-purple, nearest to RHS 71B; apex is white, RHS 155A. Fading, upper surface — Not fading. Fading, lower surface — Not fading. Venation — Densely reticulate. Venation color, fully opened, upper surface — Central lobe — Greyed-purple, in between RHS N186C and N186D, and suffused with red-purple towards the base, nearest to RHS 61A. Lateral lobes — Red-purple, nearest to RHS 70B; apex is white, RHS 155A. Venation color, fully opened, lower surface — Central lobe — Red-purple, nearest to RHS 64A, and fading to a lighter shade of red-purple towards the base, in between RHS 72B and 72C. Lateral lobes — Red-purple, nearest to RHS 71B; apex is white, RHS 155A.

*Callosities*.—Dimensions — 1.3 cm long and 0.8 cm wide, on average. Color — Red-purple, in between RHS N74A and N74B.

*Spurs*.—Quantity — Average of 1. Length — Approximately 0.9 cm. Diameter — Approximately 0.2 cm. Vertical height — Approximately 0.6 cm, at the base. Shape — Short triangular. Apex — Bluntly acute. Base — Broad cuneate. Pubescence, texture and luster — Glabrous, smooth, and matte. Color — Purple, nearest to RHS 76C, and striped with a darker shade of purple, nearest to RHS 76A.

*Sepals*.—Quantity — Average of 3 unfused sepals. Arrangement — One dorsal sepal and two lateral sepals. Length — Dorsal sepal — Approximately 4.9 cm. Lateral sepals — Approximately 5.2 cm. Width — Dorsal sepal — Approximately 4.3 cm. Lateral sepals — Approximately 4.8 cm. Shape — Dorsal sepal — Broad ovate. Lateral sepals — Broad ovate. Apex — Dorsal sepal — Obtuse. Lateral sepals — Obtuse. Base — Dorsal sepal — Cuneate. Lateral sepals — Cuneate. Margin — Dorsal sepal — Entire; very slightly undulated. Lateral sepals — Entire; not undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Purple, nearest to RHS N78C; heavily dotted and blotched with a darker shade of purple, in between RHS N78A and N78B but closest to RHS N78A. Lateral sepals — Purple, nearest to RHS N78C; heavily dotted and blotched with a darker shade of purple, in between RHS N78A and N78B but closest to RHS N78B. Color when opening, lower surface — Dorsal sepal — Purple, nearest to RHS N78C; heavily dotted and blotched with a darker shade of purple, nearest to RHS N78A. Lateral sepals — Purple, nearest to RHS N78C; heavily dotted and blotched with a darker shade of purple, nearest to RHS N78A. Color when fully opened, upper surface — Dorsal sepal — Purple, nearest to RHS N78B. Lateral sepals — Purple, nearest to RHS N78B. Color when fully opened, lower surface — Dorsal sepal — Purple, nearest to RHS N78B. Lateral sepals — Purple, nearest to RHS N78B. Fading, upper surface — Not fading. Fading, lower surface — Not fading. Venation — Densely reticulate. Venation color, fully opened, upper surface — Dorsal sepal — Purple, in between RHS N78A and NN78A. Lateral sepals — Red-purple, nearest to RHS 72A. Venation color, fully opened, lower surface — Dorsal sepal — Purple, in between RHS N78A and NN78A. Lateral sepals — Purple, in between RHS N78A and NN78A.

*Pedicels*.—Length — Approximately 5.7 cm. Diameter — Approximately 0.4 cm. Angle — Approximately 70 degree angle to peduncle axis. Strength — Moderate. Texture — Glabrous, axially angled with 5 "ribs", axially twisted (due to resupination). Luster — Glossy. Color — Purple, nearest to RHS N78A.

*Bract*.—Quantity — One bract present at the base of each pedicel. Shape — Broad ovate; folded around the base of each pedicel. Dimensions — Average of 1.0 cm long and 1.2 cm wide. Apex — Broad acute. Base — Broad cuneate. Margins — Entire. Color, both surfaces — Yellow-green, nearest to RHS 144B.

Reproductive organs:

*Column*.—Length — Approximately 0.5 cm. Diameter — Approximately 0.7 cm. Color — Purple, nearest to RHS 77C, with a more intense colored central stripe, nearest to RHS NN78B.

*Ovary*.—Position — Inferior. Diameter — Approximately 0.2 cm. Color — Yellow-green, RHS 150C.

*Pollinia color*.—Greyed-orange, nearest to RHS 167A.

Seed and fruit: No fruit and seed production has been detected to date.

Comparison With the Parent Plants

Plants of the new cultivar 'SPCDW1519' differ from the *Vanda* seed parent, 'MNSR' (not patented), by the characteristics described in Table 1.

TABLE 1

| Characteristic | 'SPCDW1519' | 'MNSR' |
|---|---|---|
| General coloration of the petals and sepals when fully opened. | Purple. | Blue. |
| Plant height. | Taller than 'MNSR'. | Shorter than 'SPCDW1519'. |
| Inflorescence height. | Taller than 'MNSR'. | Shorter than 'SPCDW1519'. |
| Flower size. | Smaller than 'MNSR'. | Larger than 'SPCDW1519'. |
| Plant vigor. | More vigorous; easier to cultivate and quicker to flower when compared 'MNSR'. | Less vigorous; more difficult to cultivate and slower to to flower when compared to 'SPCDW1519'. |

Plants of the new cultivar 'SPCDW1519' differ from the *Vanda* pollen parent, '70BL' (not patented), by the characteristics described in Table 2.

TABLE 2

| Characteristic | 'SPCDW1519' | '70BL' |
|---|---|---|
| General coloration of the petals and sepals when fully opened. | Purple. | Blue. |
| Plant height. | Shorter than '70BL'. | Taller than 'SPCDW1519'. |
| Flower size. | Smaller than '70BL'. | Larger than 'SPCDW1519'. |
| Plant vigor. | More vigorous; easier to cultivate and quicker to flower when compared to '70BL'. | Less vigorous; more difficult to cultivate and slower to flower when compared to 'SPCDW1519'. |

Comparison With the Most Similar *Vanda* Cultivar Known to the Inventor

Plants of the new cultivar 'SPCDW1519' are most similar to the cultivar, *Vanda* 'Princess Mikasa Pink' (not patented). A comparison of 'SPCDW1519' with *Vanda* 'Princess Mikasa Pink' is described in Table 3.

TABLE 3

| Characteristic | 'SPCDW1519' | 'Princess Mikasa Pink' |
|---|---|---|
| Length of foliage. | Shorter than 'Princess Mikasa Pink'. | Longer than 'SPCDW1519'. |
| General coloration of the foliage. | Darker green than 'Princess Mikasa Pink'. | Lighter green than 'SPCDW1519'. |
| Flower size. | Smaller than 'Princess Mikasa Pink'. | Larger than 'SPCDW1519'. |

TABLE 3-continued

| Characteristic | 'SPCDW1519' | 'Princess Mikasa Pink' |
|---|---|---|
| General coloration of the petals and sepals when fully opened. | Purple. | Pink. |
| Width of labellum. | Wider than 'Princess Mikasa Pink'. | More narrow than 'SPCDW1519'. |
| Lateral lobes of labellum; general coloration when fully open. | Darker shade of red-purple. | Lighter shade of red-purple. |
| Column size. | Larger than 'Princess Mikasa Pink'. | Smaller than 'SPCDW1519'. |

That which is claimed is:

1. A new and distinct variety of *Vanda* plant named 'SPCDW1519', substantially as described and illustrated herein.

* * * * *